(12) United States Patent
Sheppard et al.

(10) Patent No.: US 10,060,861 B2
(45) Date of Patent: Aug. 28, 2018

(54) TECHNOLOGIES FOR IDENTIFYING DEFECTS

(71) Applicant: Sunspring America, Inc., Vanderbilt, MI (US)

(72) Inventors: Scott Steven Sheppard, Brutus, MI (US); James Richard Lambdin, Vanderbilt, MI (US)

(73) Assignee: SUNSPRING AMERICA, INC., Vanderbuilt, MI (US)

(*) Notice: Subject to any disclaimer, the term of this patent is extended or adjusted under 35 U.S.C. 154(b) by 0 days.

(21) Appl. No.: 15/854,497

(22) Filed: Dec. 26, 2017

(65) Prior Publication Data

US 2018/0195976 A1    Jul. 12, 2018

Related U.S. Application Data

(60) Provisional application No. 62/444,566, filed on Jan. 10, 2017.

(51) Int. Cl.
  *G01N 21/00*     (2006.01)
  *G01N 21/952*    (2006.01)
  *G01N 21/88*     (2006.01)

(52) U.S. Cl.
  CPC ....... *G01N 21/952* (2013.01); *G01N 21/8806* (2013.01); *G01N 2021/8809* (2013.01); *G01N 2201/06113* (2013.01)

(58) Field of Classification Search
  CPC ............. G01N 21/952; G01N 21/8806; G01N 2201/06113; G01N 2021/8809; G01N 15/0205; G01N 15/0211; G01N 2021/8861; G01N 21/55; G01N 2291/102; G01N 2291/2634; B23K 26/03; G01B 11/2425; G01B 11/306; G02B 21/0032; G21C 17/017
  See application file for complete search history.

(56) References Cited

U.S. PATENT DOCUMENTS

| | | | |
|---|---|---|---|
| 3,746,575 A * | 7/1973 | Arnaudin, Jr. et al. | ...................... G10N 21/952 118/670 |
| 3,822,945 A * | 7/1974 | Robinson | ............. G01N 21/952 250/559.42 |
| 4,203,673 A * | 5/1980 | Buckson | ............. G01N 21/952 209/587 |
| 4,315,688 A * | 2/1982 | Pryor | .................... G01B 11/22 356/237.1 |

(Continued)

FOREIGN PATENT DOCUMENTS

| WO | WO2005065246 | 7/2005 |
|---|---|---|
| WO | WO2010006197 | 1/2010 |

*Primary Examiner* — Mohamed K Amara
(74) *Attorney, Agent, or Firm* — Dentons US LLP; Brian R. McGinley; Roman Tsibulevskiy

(57) ABSTRACT

A method comprises: directing a laser beam onto a side of a tube, wherein the side includes a defect; moving the tube with respect to the laser beam such that the laser beam beams onto the defect; sensing a reflection of the laser beam from the side based on the defect; computationally identifying a change between the laser beam and the reflection; computationally acting based on the change. The side can be internal or external. In other implementations, the laser beam is moved with respect to the tube such that the laser beam beams onto the defect.

26 Claims, 8 Drawing Sheets

(56) References Cited

U.S. PATENT DOCUMENTS

| | | | | |
|---|---|---|---|---|
| 4,410,278 A * | 10/1983 | Makihira | G01N 21/952 | 250/559.07 |
| 4,532,723 A * | 8/1985 | Kellie | G01B 11/00 | 209/579 |
| 4,644,394 A * | 2/1987 | Reeves | G01N 21/952 | 33/199 B |
| 4,734,766 A * | 3/1988 | Shiozumi | G01B 11/024 | 356/608 |
| 5,007,291 A * | 4/1991 | Walters | G01N 29/043 | 226/176 |
| 5,012,117 A * | 4/1991 | Karafa | G01N 21/952 | 250/559.16 |
| 5,273,474 A * | 12/1993 | Oshima | H01T 21/02 | 219/121.64 |
| 5,479,252 A | 12/1995 | Worster et al. | | |
| 5,646,724 A * | 7/1997 | Hershline | G01N 21/952 | 250/223 R |
| 5,936,725 A * | 8/1999 | Pike | G01B 11/08 | 348/125 |
| 6,052,911 A * | 4/2000 | Davis | G01B 11/27 | 33/286 |
| 6,091,834 A * | 7/2000 | Bradburn | G01N 21/8806 | 250/559.02 |
| 6,124,926 A | 9/2000 | Ogawa et al. | | |
| 6,169,600 B1 * | 1/2001 | Ludlow | A24C 5/3412 | 131/905 |
| 6,610,953 B1 | 8/2003 | Tao et al. | | |
| 6,800,859 B1 | 10/2004 | Shishido et al. | | |
| 7,385,688 B1 * | 6/2008 | Kadkly | G01N 21/8806 | 356/237.4 |
| 8,363,101 B2 * | 1/2013 | Gschwendtner | G01B 11/2433 | 348/135 |
| 8,860,952 B2 * | 10/2014 | Bondurant | G01B 11/24 | 356/602 |
| 8,890,023 B2 | 11/2014 | Dorsch et al. | | |
| 9,134,232 B1 * | 9/2015 | Segall | G01N 21/952 | |
| 9,523,648 B2 | 12/2016 | Urano et al. | | |
| 9,588,056 B2 * | 3/2017 | Fontaine | G01N 21/89 | |
| 2003/0210391 A1 | 11/2003 | Uto et al. | | |
| 2003/0227617 A1 | 12/2003 | Yoshida et al. | | |
| 2004/0011773 A1 * | 1/2004 | Fritz | B23K 26/03 | 219/121.83 |
| 2004/0262529 A1 | 12/2004 | Yoshida et al. | | |
| 2005/0264797 A1 | 12/2005 | Nakano et al. | | |
| 2006/0062343 A1 * | 3/2006 | Perng | G01N 21/952 | 376/251 |
| 2008/0186481 A1 * | 8/2008 | Chen | G01N 21/8803 | 356/237.1 |
| 2009/0002695 A1 * | 1/2009 | Saito | G01N 21/8806 | 356/237.4 |
| 2009/0122303 A1 | 5/2009 | Nakano et al. | | |
| 2010/0085561 A1 | 4/2010 | Kamiyama et al. | | |
| 2010/0086003 A1 | 4/2010 | Pfitzner et al. | | |
| 2010/0091812 A1 | 4/2010 | Louban et al. | | |
| 2010/0123080 A1 | 5/2010 | Andres et al. | | |
| 2011/0296923 A1 * | 12/2011 | Cataldo | G01N 29/043 | 73/632 |
| 2012/0008143 A1 * | 1/2012 | Ihlefeld | G01N 15/0205 | 356/335 |
| 2012/0127462 A1 * | 5/2012 | Wakatake | G01N 21/952 | 356/237.2 |
| 2012/0182023 A1 * | 7/2012 | Zhang | G01M 11/3109 | 324/501 |
| 2014/0139233 A1 * | 5/2014 | Jeong | G01R 31/11 | 324/520 |
| 2014/0175071 A1 | 6/2014 | Pfitzner et al. | | |
| 2016/0144452 A1 | 5/2016 | Liou et al. | | |

* cited by examiner

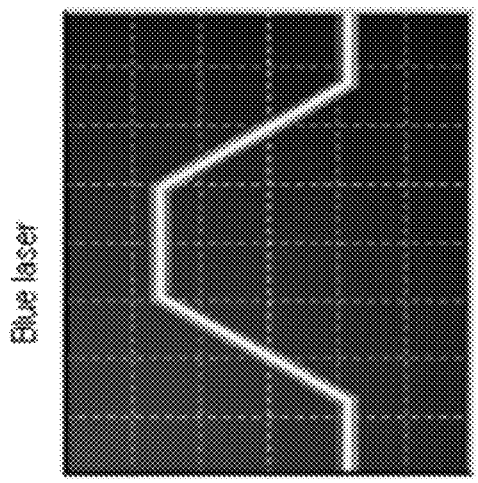
Fig. 5A
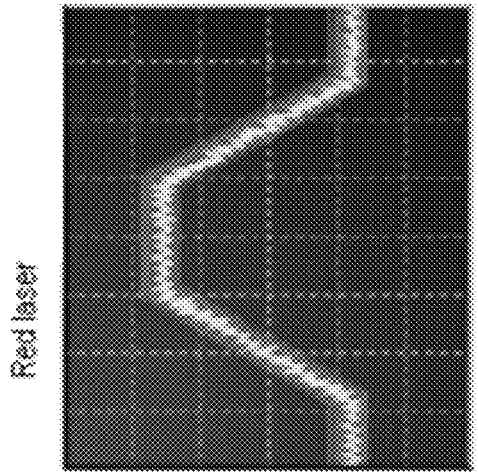
Fig. 5B

TECHNOLOGIES FOR IDENTIFYING DEFECTS

CROSS-REFERENCE TO RELATED APPLICATIONS

This application claims a benefit of U.S. Provisional Patent Application 62/444,566 filed on Jan. 10, 2017, which is herein incorporated by reference for all purposes.

TECHNICAL FIELD

This disclosure relates to identifying defects.

BACKGROUND

In this disclosure, where a document, an act, and/or an item of knowledge is referred to and/or discussed, then such reference and/or discussion is not an admission that the document, the act, and/or the item of knowledge and/or any combination thereof was at a priority date, publicly available, known to a public, part of common general knowledge, and/or otherwise constitutes any prior art under any applicable statutory provisions; and/or is known to be relevant to any attempt to solve any problem with which this disclosure is concerned with. Further, nothing is disclaimed.

Sometimes, a tube, such as a copper tube or a copper-alloy tube, is unintentionally manufactured with a defect, such as a hole, a weak spot, a dent, a notch, a flaw, a scratch, a depression, a projection, a deformity, or others. In certain cases, the defect renders the tube undesired for use, such as due to the tube being unsafe because of the defect or inoperative because of the defect. As such, the tube is tested, such as randomly, for a presence of the defect.

One way the tube is tested for the defect is via an American Society for Testing and Materials (ASTM) Standard E243, which describes a procedure for an electromagnetic (eddy current) examination of the tube. For example, as illustrated in FIGS. 1 and 2, this examination involves a single-element eddy current test (ECT) probe, which includes a coil of a conductive wire that is excited with an alternating current (AC). During such excitement, the coil produces an alternating magnetic field around itself in a direction ascertained by a right-hand rule. The alternating magnetic field oscillates at a same frequency as the AC passing through the coil. Consequently, when the coil is positioned in a close proximity to a conductive material, such as the tube, a current, such as an eddy current, opposed to the AC in the coil is induced in the conductive material. As such, a variation in an electrical conductivity of the conductive material or a magnetic permeability of the conductive material, along with the presence of the defect cause a change in the current, including a change in a phase of the current and an amplitude of the current. The change in the current is detected by a sensor that senses a change in an impedance of the coil. The change in the impedance of the coil is a sign of the presence of the defect.

Although testing in accordance with the ASTM Standard E243 is useful, there are situations when the presence of the defect is still missed. As such, periodically, the tube is intentionally manufactured with the defect and then tested in accordance with the ASTM Standard E243, in order to ensure that testing in accordance with the ASTM Standard E243 is being correctly conducted. However, this methodology is time-consuming to perform and costly to manage. Additionally, if the tube is lubricated with a lubricant, then testing in accordance with the ASTM Standard E243 becomes more complicated due to an electromagnetic interference between the alternating magnetic field and the lubricant. The electromagnetic interference makes testing in accordance with the ASTM Standard E243 time-consuming to perform and costly to manage. Moreover, if the tube varies in shape, cross-section, size, material, or other tube characteristics, then testing in accordance with the ASTM Standard E243 becomes more complicated because, for each such tube variation, an appropriate coil is needed, which is time-consuming to perform and costly to manage. Accordingly, there is a desire to address at least one of such inefficiencies.

SUMMARY

This disclosure at least partially addresses at least one of above inefficiencies. However, this disclosure can prove useful to other technical areas. Therefore, various claims recited below should not be construed as necessarily limited to addressing any of the above inefficiencies In an embodiment, a method comprises: directing a laser beam onto an outer side of a tube, wherein the outer side includes a defect; moving the tube with respect to the laser beam such that the laser beam beams onto the defect; sensing a reflection of the laser beam from the outer side based on the defect; computationally identifying a change between the laser beam and the reflection; computationally acting based on the change.

In an embodiment, a method comprises: directing a laser beam onto an inner side of a tube, wherein the inner side includes a defect; moving the tube with respect to the laser beam such that the laser beam beams onto the defect; sensing a reflection of the laser beam from the inner side based on the defect; computationally identifying a change between the laser beam and the reflection; computationally acting based on the change.

In an embodiment, a method comprises: directing a laser beam onto an outer side of a tube, wherein the outer side includes a defect; moving the laser beam with respect to the tube such that the laser beam beams onto the defect; sensing a reflection of the laser beam from the outer side based on the defect; computationally identifying a change between the laser beam and the reflection; computationally acting based on the change.

In an embodiment, a method comprises: directing a laser beam onto an inner side of a tube, wherein the inner side includes a defect; moving the laser beam with respect to the tube such that the laser beam beams onto the defect; sensing a reflection of the laser beam from the inner side based on the defect; computationally identifying a change between the laser beam and the reflection; computationally acting based on the change.

In an embodiment, a system comprises: a processor; a sensor coupled to the processor; a laser scanner coupled to the processor, wherein the laser scanner is configured to output a laser beam; and a tube straightener coupled to the processor, wherein the tube straightener is configured to move a tube with an outer side having a defect such that (1) the laser scanner is able to direct the laser beam onto the defect, (2) the sensor is able to sense a reflection of the laser beam from the outer side based on the defect, (3) the processor is able to identify a change between the laser beam and the reflection, and (4) the processor is able to take an action based on the change.

This disclosure is embodied in various forms illustrated in a set of accompanying illustrative drawings. Note that variations are contemplated as being a part of this disclosure, limited only by a scope of various claims recited below.

DESCRIPTION OF DRAWINGS

The set of accompanying illustrative drawings shows various example embodiments of this disclosure. Such drawings are not to be construed as necessarily limiting this disclosure. Like numbers and/or similar numbering scheme can refer to like and/or similar elements throughout.

FIGS. 5A-5B show a pair of charts for a pair of laser beams of an embodiment of a method of identifying a defect according to this disclosure.

DETAILED DESCRIPTION OF PREFERRED EMBODIMENTS

Figure 1:
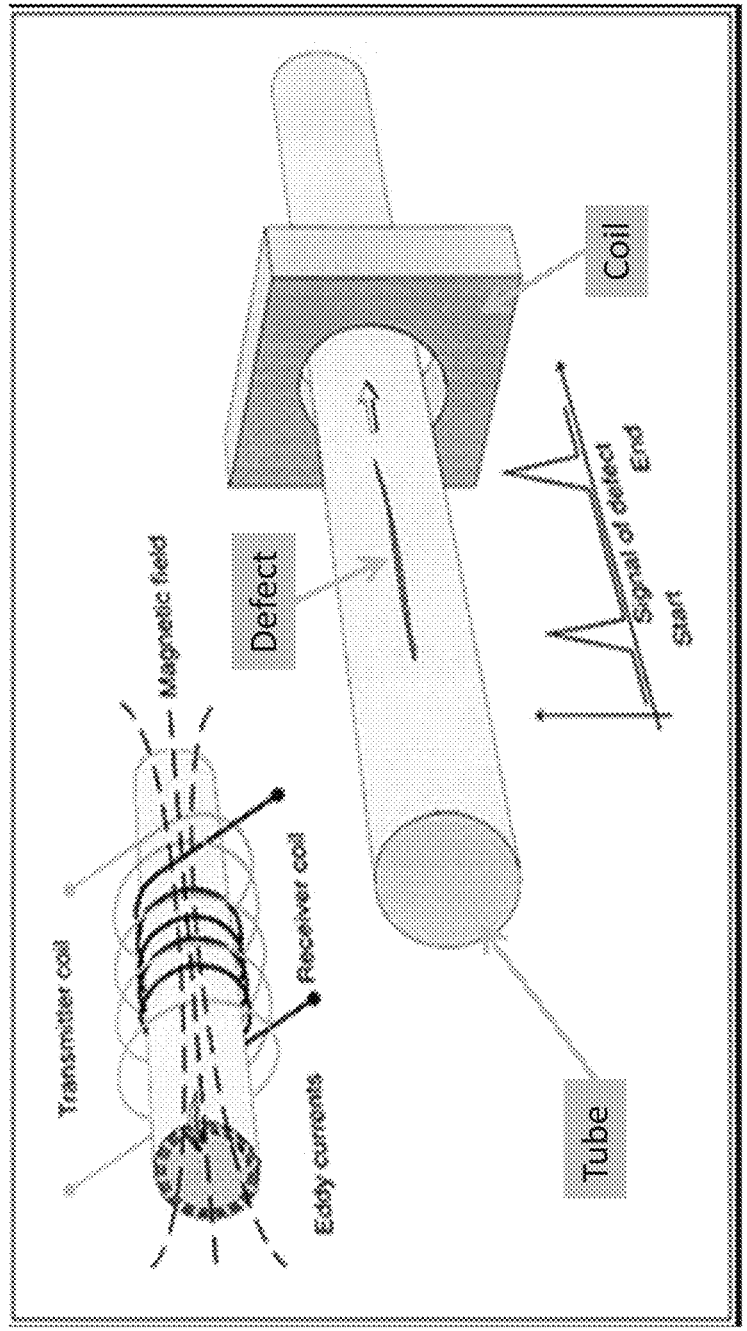
FIG. 1 shows an ECT probe being used to identify a defect in a tube.

This disclosure is now described more fully with reference to the set of accompanying illustrative drawings, in which example embodiments of this disclosure are shown. This disclosure can be embodied in many different forms and should not be construed as necessarily being limited to the example embodiments disclosed herein. Rather, the example embodiments are provided so that this disclosure is thorough and complete, and fully conveys various concepts of this disclosure to those skilled in a relevant art.

Features described with respect to certain example embodiments can be combined and sub-combined in and/or with various other example embodiments. Also, different aspects and/or elements of example embodiments, as disclosed herein, can be combined and sub-combined in a similar manner as well. Further, some example embodiments, whether individually and/or collectively, can be components of a larger system, wherein other procedures can take precedence over and/or otherwise modify their application. Additionally, a number of steps can be required before, after, and/or concurrently with example embodiments, as disclosed herein. Note that any and/or all methods and/or processes, at least as disclosed herein, can be at least partially performed via at least one entity in any manner.

Various terminology used herein can imply direct or indirect, full or partial, temporary or permanent, action or inaction. For example, when an element is referred to as being "on," "connected" or "coupled" to another element, then the element can be directly on, connected or coupled to the other element and/or intervening elements can be present, including indirect and/or direct variants. In contrast, when an element is referred to as being "directly connected" or "directly coupled" to another element, there are no intervening elements present.

Although the terms first, second, etc. can be used herein to describe various elements, components, regions, layers and/or sections, these elements, components, regions, layers and/or sections should not necessarily be limited by such terms. These terms are used to distinguish one element, component, region, layer or section from another element, component, region, layer or section. Thus, a first element, component, region, layer, or section discussed below could be termed a second element, component, region, layer, or section without departing from various teachings of this disclosure.

Various terminology used herein is for describing particular example embodiments and is not intended to be necessarily limiting of this disclosure. As used herein, various singular forms "a," "an" and "the" are intended to include various plural forms as well, unless a context clearly indicates otherwise. Various terms "comprises," "includes" and/or "comprising," "including" when used in this specification, specify a presence of stated features, integers, steps, operations, elements, and/or components, but do not preclude the presence and/or addition of one or more other features, integers, steps, operations, elements, components, and/or groups thereof.

As used herein, a term "or" is intended to mean an inclusive "or" rather than an exclusive "or." That is, unless specified otherwise, or clear from context, "X employs A or B" is intended to mean any of a set of natural inclusive permutations. That is, if X employs A; X employs B; or X employs both A and B, then "X employs A or B" is satisfied under any of the foregoing instances.

Example embodiments of this disclosure are described herein with reference to illustrations of idealized embodiments (and intermediate structures) of this disclosure. As such, variations from various illustrated shapes as a result, for example, of manufacturing techniques and/or tolerances, are to be expected. Thus, various example embodiments of this disclosure should not be construed as necessarily limited to various particular shapes of regions illustrated herein, but are to include deviations in shapes that result, for example, from manufacturing.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing, and/or other any other types of manufacturing. For example, some manufacturing processes include three dimensional (30) printing, laser cutting, computer numerical control routing, milling, pressing, stamping, vacuum forming, hydroforming, injection molding, lithography, and so forth.

Any and/or all elements, as disclosed herein, can be and/or include, whether partially and/or fully, a solid, including a metal, a mineral, an amorphous material, a ceramic, a glass ceramic, an organic solid, such as wood and/or a polymer, such as rubber, a composite material, a semiconductor, a nanomaterial, a biomaterial and/or any combinations thereof. Any and/or all elements, as disclosed herein, can be and/or include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, opaqueness, luminescence, reflection, phosphorescence, anti-reflection and/or holography, a photo-sensitive coating, an electronic and/or thermal property coating, such as for passivity, insulation, resistance or conduction, a magnetic coating, a water-resistant and/or waterproof coating, a scent coating and/or any combinations thereof. Any and/or all elements, as disclosed herein, can be rigid, flexible, and/or any other combinations thereof. Any and/or all elements, as disclosed herein, can be identical and/or different from each other in material, shape, size, color and/or any measurable dimension, such as length, width, height, depth, area, orientation, perimeter, volume, breadth, density, temperature, resistance, and so forth.

Unless otherwise defined, all terms (including technical and scientific terms) used herein have the same meaning as commonly understood by one of ordinary skill in an art to which this disclosure belongs. Various terms, such as those defined in commonly used dictionaries, should be interpreted as having a meaning that is consistent with a meaning in a context of a relevant art and should not be interpreted in an idealized and/or overly formal sense unless expressly so defined herein.

Furthermore, relative terms such as "below," "lower," "above," and "upper" can be used herein to describe one element's relationship to another element as illustrated in the set of accompanying illustrative drawings. Such relative terms are intended to encompass different orientations of illustrated technologies in addition to an orientation depicted in the set of accompanying illustrative drawings. For example, if a device in the set of accompanying illustrative drawings were turned over, then various elements described as being on a "lower" side of other elements would then be oriented on "upper" sides of other elements. Similarly, if a device in one of illustrative figures were turned over, then various elements described as "below" or "beneath" other elements would then be oriented "above" other elements. Therefore, various example terms "below" and "lower" can encompass both an orientation of above and below.

As used herein, a term "about" and/or "substantially" refers to a +/−10% variation from a nominal value/term. Such variation is always included in any given value/term provided herein, whether or not such variation is specifically referred thereto.

If any disclosures are incorporated herein by reference and such disclosures conflict in part and/or in whole with this disclosure, then to an extent of a conflict, if any, and/or a broader disclosure, and/or broader definition of terms, this disclosure controls. If such disclosures conflict in part and/or in whole with one another, then to an extent of a conflict, if any, a later-dated disclosure controls.

Figure 3:
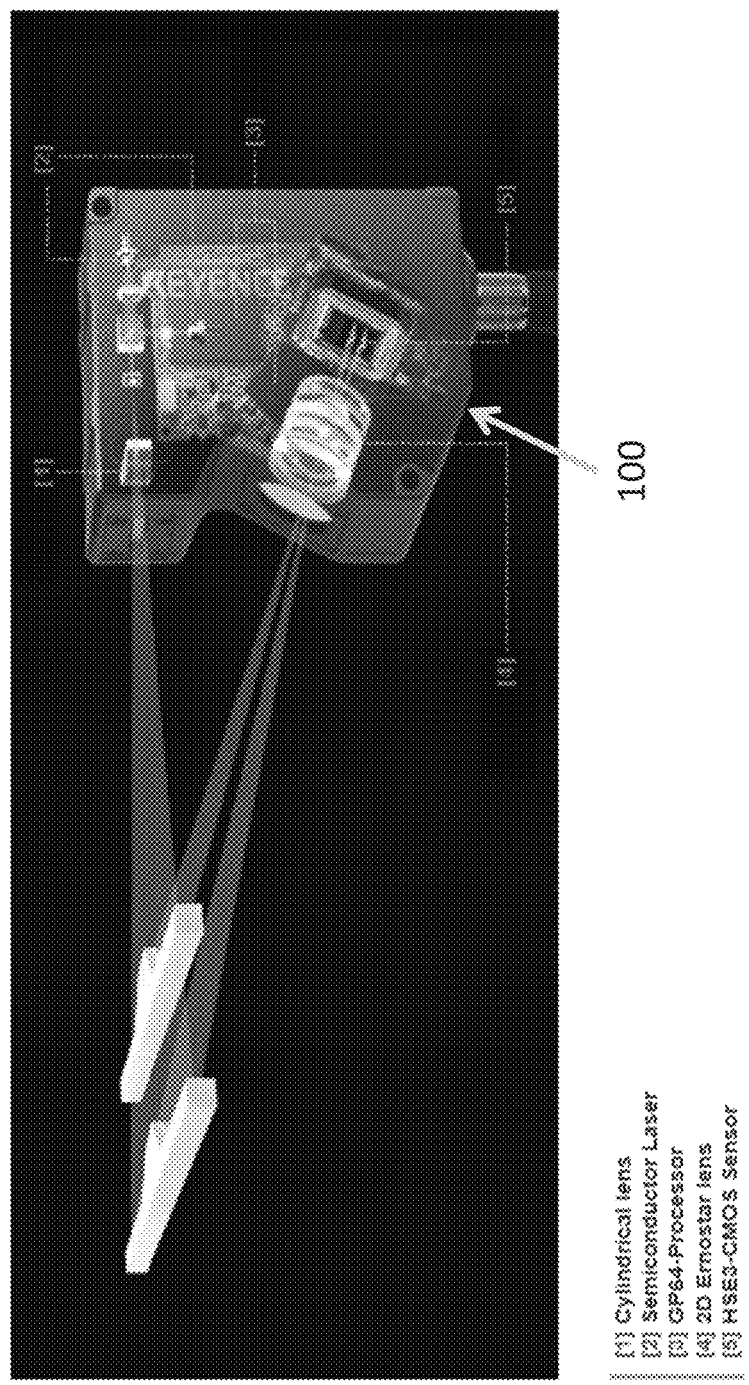
FIG. 3 shows a schematic view of an embodiment of a laser scanner according to this disclosure.
Figure 4:
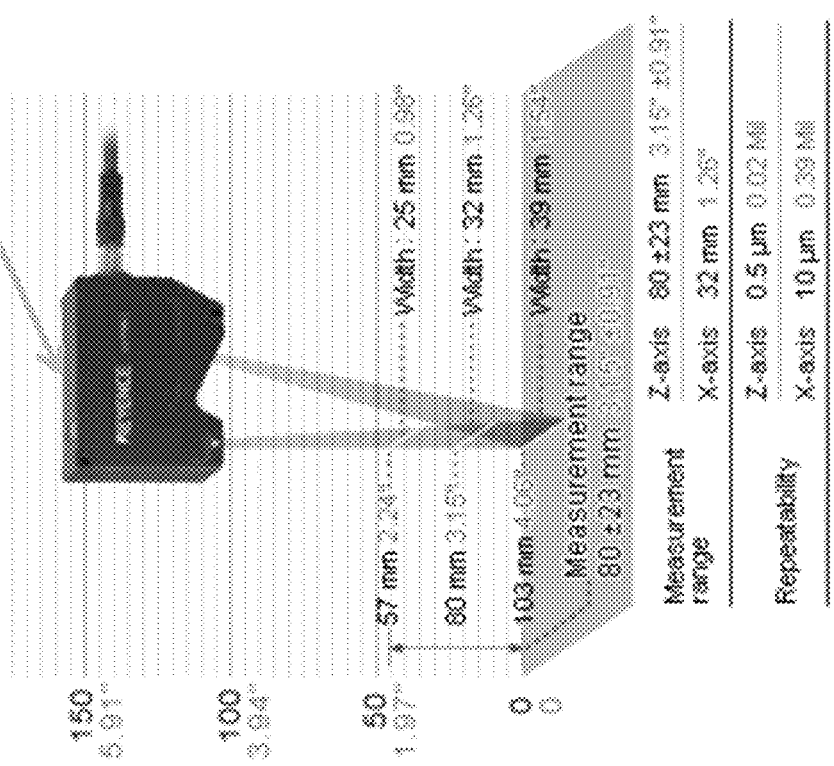
FIG. 4 shows a perspective view of an embodiment of a laser scanner according to this disclosure.

FIG. 3 shows a schematic view of an embodiment of a laser scanner according to this disclosure. FIG. 4 shows a perspective view of an embodiment of a laser scanner according to this disclosure. A laser scanner 100, such as a Keyence LJ-V7000 Series, includes a cylindrical lens 1 (or any other suitable lens), a semiconductor laser 2 (or any other suitable laser), a GP64 parallel processor 3 (or any other suitable processor), a 2D Ernostar lens 4 (or any other suitable lens), and a HSE3-CMOS sensor 5 (or any other suitable sensor). The laser scanner 100 is powered via a power source, such as mains electricity, a battery, or others. The semiconductor laser 2 is expanded into a line or a box or dot of any shape/size and directed to an outer side of a tube (shown as a white object on left). For example, the box can be circular, oval, ovoid, triangular, trapezoidal, square, rectangular, pentagonal, octagonal, hexagonal, or others, whether open or closed shaped, whether symmetrical or asymmetrical. Although the semiconductor laser 2 includes or is a blue laser, other laser types can be used, such as red or any other within a visible region of an electromagnetic spectrum, such as having a wavelength in a range of about 350 nanometers (nm) to about 800 nm, or 3.50×10-7 to 8.00×10-7 m at a frequency range of about 420 terahertz (THz) to about 760 THz. For example, a blue laser can have a wavelength between 360 nm and 480 nm, which a human eye can see as blue or violet. For example, a blue laser can be produced by a helium-cadmium gas laser at a wavelength 441.6 nm or by an argon-ion laser at a wavelength from about 455 nm to about 490 nm. For example, The HSE3-CMOS sensor 5 may be pre-calibrated with a traceability certificate. Note that multiple laser scanners 100 can be used.

The semiconductor laser 2 is then diffusely reflected from the outer side. This reflected light is formed on the HSE3-CMOS sensor 5. As such, by computationally detecting changes in a position and/or shape of this reflected light, a computer, which is in signal communication with the laser scanner 100, whether in a wired or wireless manner, can measure a position of a point along the outer side, where the point is indicative of a defect of the outer side. For example, since this reflected light reflects/comes back at different speeds, then such data is used to computationally interpret as high and low spots in the outer side of the tube. Note that this includes many points, including defects, if any, along the outer side, whether along a single plane of the outer side or a plurality of planes of the outer side. As such, a map of the outer side can be created, with maps the defect on the outer side. However, as noted herein, when the tube is hollow and includes an inner side, then similar methodology can be employed. Further, note that such example of the laser scanner 100 is not limiting and other laser scanners or differently configured laser scanners can be used, whether alternatively or additionally, in any technical environment, including tube manufacturing or testing for any purpose, such as fluid conduction, whether the fluid is a liquid, a gas, or any other fluid. Some of such purposes include plumbing (e.g. cold/hot water, steam, oil, beverages, crude, etc.), heating, ventilation, and air conditioning (HVAC), wire/cable conduits, machine parts/industrial systems (e.g. factory machines, vehicles etc.), medical tubing/devices/implantables, food grade tubing (e.g. straws etc.), weapons (barrels, missiles, vehicles, etc.), shipbuilding, sports, or others, although note that such tubing does not need to be hollow and can be internally solid.

Figure 2:
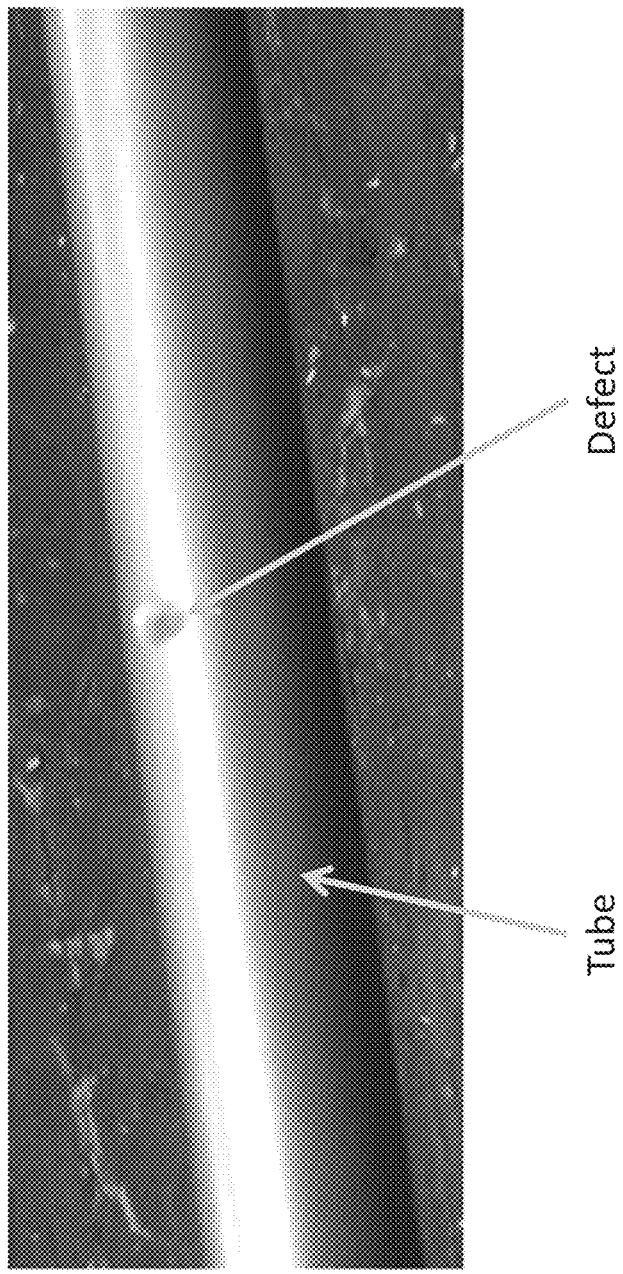
FIG. 2 shows a defect in a copper tube.

With respect to the tube, as shown in FIGS. 1 and 2, any tube can be used, whether internally solid or internally hollow, as noted above. For example, at least the outer side can include a metal, a composite, or an alloy, whether ferrous or non-ferrous. For example, the metal, the composite, or the alloy can include copper, aluminum, iron, steel, gold, silver, lithium, nickel, cobalt, manganese, chromium, bronze, zinc, or others, including a rare-earth metal, such as neodymium, yttrium, or others. At least the outer side may have a smooth surface or a textured surface, including threads, knurling, maters/interlocks, or others. At least the outer side may be longitudinally or laterally rectilinear, sinusoidal, arcuate, acutely/obtusely angled, zigzag, pulsating, or any other longitudinally extending shape or laterally extending shape, including any outward/inward depression/projection. At least the outer side may be structurally solid or structurally perforated/latticed/interstitial/slitted. At least the outer side can include a surface that is coated, such as for a structural integrity enhancement purpose. At least the outer side can be electrically conductive or thermally conductive, whether naturally through material or via adding a coating. At least the outer side can be opaque, transparent, or translucent, yet still be sufficiently reflective for use with the laser scanner 100, such as via being coated with a laser beam reflecting coating. At least the outer side may be of any color, such as gold, silver, red, green, brown, black, white, orange, purple, or others. In terms of tubular cross-section, the tube may have any cross-section, such as circular, oval, ovoid, triangular, square, rectangular, trapezoidal, pentagonal, octagonal, hexagonal, or others. When hollow, the tube has the inner side, which can mirror (or avoid mirroring) the outer side in any property, such as material, size, shape, orientation, surface, texture, conductivity, or others. Note that in such embodiments, the laser scanner 100 can be positioned into the tube and the inner side can be analyzed for defects, similarly to the outer side, as disclosed herein.

The tube may longitudinally extend in an open shape or a closed shape, whether symmetrical or asymmetrical. For example, the open shape can include an I-shape, an L-shape, a U-shape, a C-shape, a V-shape, or others. For example, the closed shape can include an O-shape, a O-shape, a D-shape, a square shape, a triangular shape, a rectangular shape, a parallelogram shape, a pentagon shape, or others. The tube can be a single piece or an assembly of pieces, such as via fastening, mating, magnetizing, adhering, or others. For example, the tube can be a pair of U-shaped pieces pivoted together, such as a clamshell. For example, the tube can be three C-shaped pieces interlocked together. In some embodiments, the tube may include plastic, rubber, wood, glass, or other non-metal materials. Note that the tube can include a metal and a non-metal.

For example, a method, such as for a laser surface analysis, can include directing a laser beam, such as from the laser scanner 100, onto the outer side of the tube, with the outer side including the defect, such as shown in FIG. 2. The method can include rotating, such as via a tube straightener, which may be an inline tube straightener, the tube with respect to the laser beam during the directing such that the laser beam beams onto the defect, which may be along a perimeter/circumference of the outer side, including while moving the tube past the laser scanner 100. For example, the tube straightener can include a motor or an actuator configured to move the tube, such as via pushing the tube or pulling the tube or spinning the tube or another type of force application. For example, the rotating can include a full rotation/360 degrees or less, such as less than 270 degrees, less than 180 degrees, less than 90 degrees, less than 60 degrees, or less than 45 degrees, or multiple full rotations, including movement of the tube during the rotating. For example, the rotating may be during a tube straightening process. The method can include receiving, such as via the HSE3-CMOS sensor, a reflection, such as the reflected light, of the laser beam from the outer side during the rotating based on the defect. The method can include identifying, via the computer, a change between the laser beam and the reflection. The method can include generating, via the computer, a message based on the change, with the message can be output via an output device, such as a display, a printer, a speaker, a vibrator, a smell generator, or others. For example, the message may inform if the defect is over/under a predefined length/width/depth/shape or another threshold. For example, the message can be stored in memory, such as in a log file, or a machine-based action can be taken based on the message, such as writing/marking/flagging (visible/invisible) on the outer side at the or in a close proximity of the defect, segregating or moving the tube with the defect. Note that if the tube is hollow and includes the inner side then this method can be reversed, where the laser beam is directed onto the inner side and then the inner side is rotated with respect to the laser beam, as disclosed herein.

For example, a method, such as for a laser surface analysis, can include directing a laser beam, such as from the laser scanner 100, onto the outer side of the tube, with the outer side including the defect, such as shown in FIG. 2. The method can include rotating the laser beam, such as via an articulating arm, with respect to the tube during the directing such that the laser beam beams onto the defect, which may be along a perimeter/circumference of the outer side, including while moving the laser scanner 100 past the tube. For example, the rotating can include a full rotation/360 degrees or less, such as less than 270 degrees, less than 180 degrees, less than 90 degrees, less than 60 degrees, or less than 45 degrees, or multiple full rotations, including movement of the tube during the rotating. For example, the rotating may be during a tube straightening process. The method can include receiving, such as via the HSE3-CMOS sensor, a reflection of the laser beam from the outer side during the rotating based on the defect. The method can include identifying, via the computer, a change between the laser beam and the reflection. The method can include generating, via the computer, a message based on the change, with the message can be output via an output device, such as a display, a printer, a speaker, a vibrator, a smell generator, or others. For example, the message may inform if the defect is over/under a predefined length/width/depth/shape. For example, the message can be stored in memory, such as in a log file, or a machine-based action can be taken based on the message, such as writing/marking/flagging (visible/invisible) on the outer side at the or in a close proximity of the defect, segregating or moving the tube with the defect. Note that if the tube is hollow and includes the inner side then this method can be reversed, where the laser beam is directed onto the inner side and then the laser beam is rotated with respect to the inner side, as disclosed herein.

For example, a method, such as for a laser surface analysis, can include directing a laser beam onto the outer side of the tube such that the laser beam perimetrically beams onto the outer side, such as in a closed shape generated via a plurality of the laser scanners 100, with the outer side including the defect beamed thereon via the laser beam. Such perimetrical beaming, which may be circumferential, such as in an O-shape, is to capture the outside side in full along a single point along the length of the outer side, although multiple points along the length of the outer side can be captured, such as via the lasers 100 moving with respect to the outer side or the outer side moving with respect to the laser scanners 100. For example, such directing may be during a tube straightening process. The method can include receiving, such as via the HSE3-CMOS sensor, a reflection of the laser beam from the outer side based on the defect. The method can include identifying, via the computer, a change between the laser beam and the reflection. The method can include generating, via the computer, a message based on the change, with the message can be output via an output device, such as a display, a printer, a speaker, a vibrator, an smell generator, or others. For example, the message may inform if the defect is over/under a predefined length/width/depth/shape. For example, the message can be stored in memory, such as in a log file, or a machine-based action can be taken based on the message, such as writing/marking/flagging (visible/invisible) on the outer side at the or in a close proximity of the defect, segregating or moving the tube with the defect. Note that if the tube is hollow and includes the inner side then this method can be reversed, where the laser beam is radially directed, such as in a sunray manner, onto the inner side such that a perimeter of the inner side is beamed at once along a point along a length of the inner side, as disclosed herein.

FIGS. 5A-5B show a pair of charts for a pair of laser beams of an embodiment of a method of identifying a defect according to this disclosure. Although the semiconductor laser 2 can be or include a red laser beam or a blue laser beam, in some embodiments, the semiconductor laser 2 is or includes the blue beam laser because in such embodiments, the red laser beam has a limited focus in comparison to the blue laser beam, where this limited focus results in a diffuse image of a part that contributes to measurement errors. In contrast, in such embodiments, the blue laser beam, such as due to frequency, enables a target image to be tightly focused with minimal blurring or other sources of error. For example, with blue laser technology the target image is more tightly focused and is not largely effected by a glare of copper tubing. Therefore, this can make blue laser technology a replacement for ECT testing.

Figure 6A:
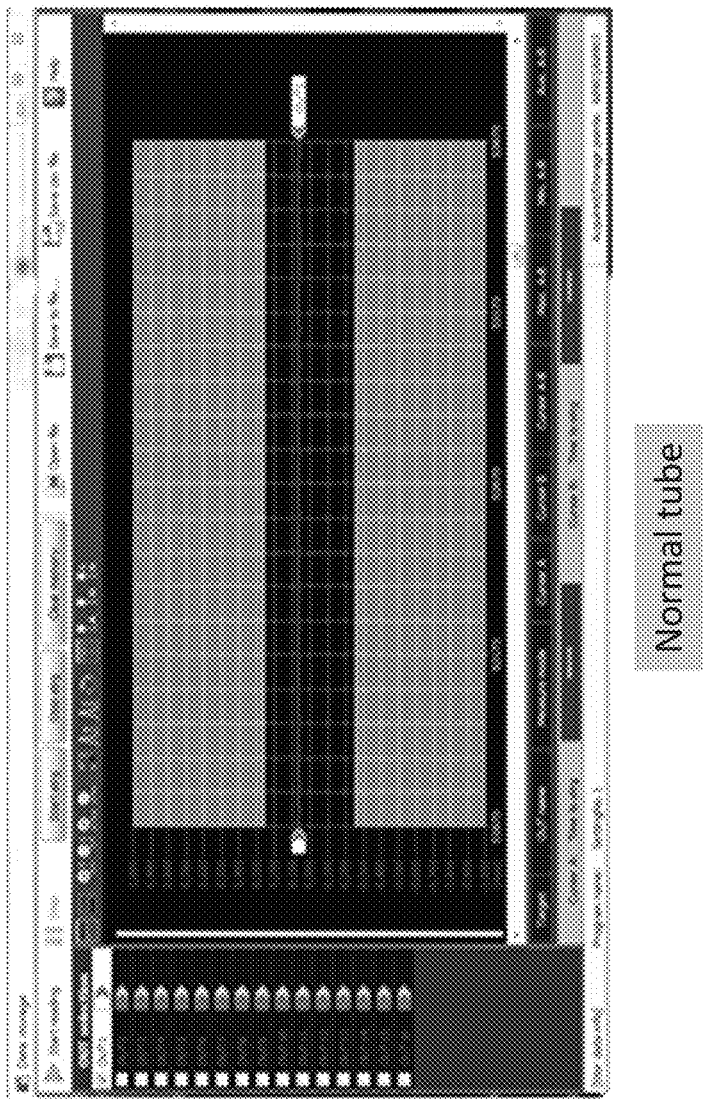
FIGS. 6A-6B show a pair of application screenshots depicting a pair of property sets for a pair of tubes according to this disclosure.
Figure 6B:
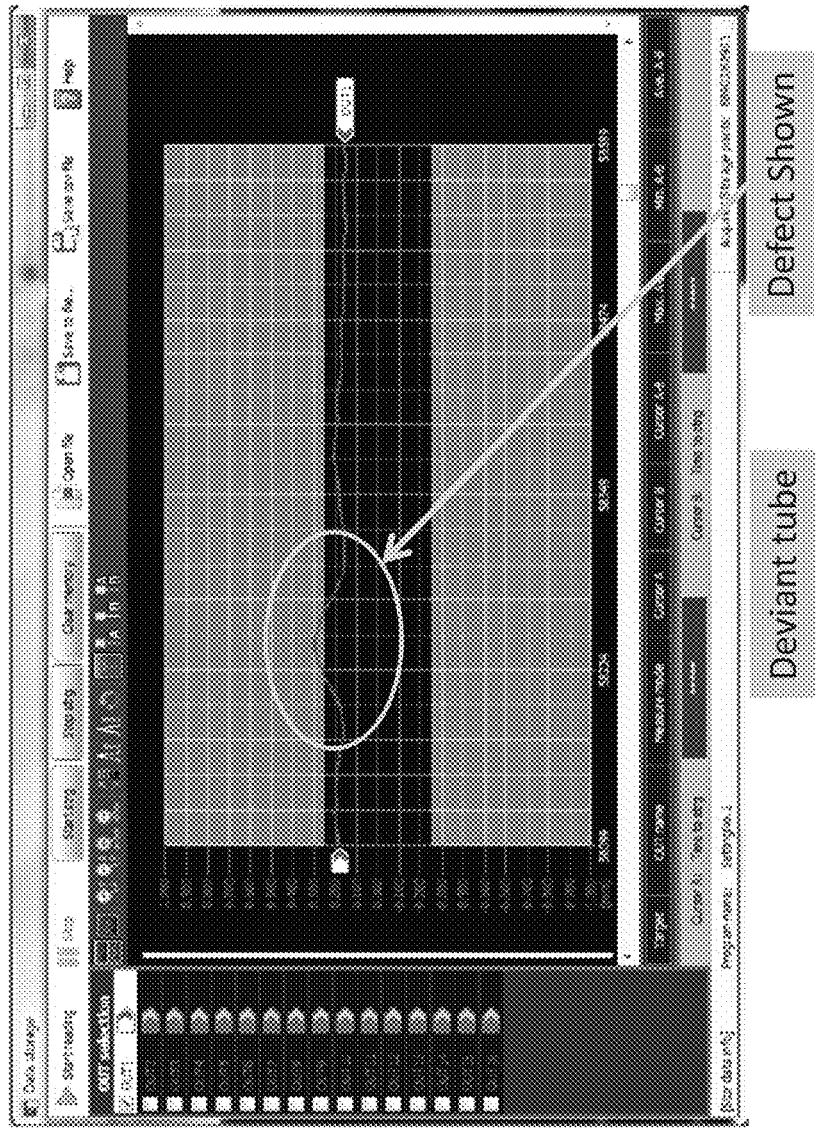

FIGS. 6A-6B show a pair of application screenshots depicting a pair of property sets for a pair of tubes according to this disclosure. The computer runs an operating system and a software application on top of the operating system. The software application is able to show a graph indicative of a lack of the presence of the defect (normal tube) and the presence of the defect (deviant tube). As shown in FIG. 6a, the lack of the presence of the defect (normal tube) is shown via a line being relatively rectilinear. In contrast, as shown in FIG. 6b, the presence of the defect (deviant tube) is shown via the line having an arcuate portion representative of the defect. Note that a sensitivity of a detection device, such as the laser scanner 100/computer combo, may be adjusted to ensure that the defect is detected.

Figure 7:
FIG. 7 shows a perspective view of an embodiment of a laser scanner coupled to a tube straightener according to this disclosure.

FIG. 7 shows a perspective view of an embodiment of a laser scanner coupled/installed/retrofitted to a tube straightener according to this disclosure. The laser scanner 100 is coupled/installed/retrofitted to the tube straightener, which may be an inline tube straightener. The coupling/installation/retrofitting may be logical (electrical, communicable, signal etc.), mechanic (attached, mounted, fastened, adhered, mated, interlocked, magnetized etc.) or others. For example, during such coupling, the tube should be rotated sufficiently enough to capture an entire perimeter/circumference of the outer side of the tube within a bandwidth of the semiconductor laser 2. For example, the tube straightener rotates the tube enough to provide a full revolution of the tube within a window of the semiconductor laser 2. For example, as the tube passes by the laser scanner 100, which may be during a tube straightening process, the tube is rotated passed the 3" inch wide laser beam and an entire outer side of the tube, such as an entire outer surface, is analyzed. For example, during laser surface analysis there may be no changeover between parts of the laser scanner 100/tube straightener. For example, at least the outer side can be lubricated with a lubricant and the laser scanner may still effectively scan. Note that such methodology/device can be employed on the inner side of the tube when the tube is hollow. As such, this demonstrates that the laser can replace the ECT test by looking for various defects on the outer side of the tube, such as an entire surface of the tube.

In some embodiments, various functions or acts can take place at a given location and/or in connection with the operation of one or more apparatuses or systems. In some embodiments, a portion of a given function or act can be performed at a first device or location, and a remainder of the function or act can be performed at one or more additional devices or locations.

The corresponding structures, materials, acts, and equivalents of all means or step plus function elements in the claims below are intended to include any structure, material, or act for performing the function in combination with other claimed elements as specifically claimed. The embodiments were chosen and described in order to best explain the principles of the disclosure and the practical application, and to enable others of ordinary skill in the art to understand the disclosure for various embodiments with various modifications as are suited to the particular use contemplated.

The diagrams depicted herein are illustrative. There can be many variations to the diagram or the steps (or operations) described therein without departing from the spirit of the disclosure. For instance, the steps can be performed in a differing order or steps can be added, deleted or modified. All of these variations are considered a part of the disclosure. It will be understood that those skilled in the art, both now and in the future, can make various improvements and enhancements which fall within the scope of the claims which follow.

The description of this disclosure has been presented for purposes of illustration and description, but is not intended to be fully exhaustive and/or limited to the disclosure in the form disclosed. Many modifications and variations in techniques and structures will be apparent to those of ordinary skill in an art without departing from a scope and spirit of this disclosure as set forth in the claims that follow. Accordingly, such modifications and variations are contemplated as being a part of this disclosure. A scope of this disclosure is defined by various claims, which include known equivalents and unforeseeable equivalents at a time of filing of this disclosure.

What is claimed is:

1. A method comprising:
   directing a laser beam onto an outer side of a tube, wherein the outer side includes a defect;
   moving the tube with respect to the laser beam such that the laser beam beams onto the defect, wherein the moving includes rotating the tube, wherein the moving is via a tube straightener;
   sensing a reflection of the laser beam from the outer side based on the defect;
   computationally identifying a change between the laser beam and the reflection;
   computationally acting based on the change.

2. The method of claim 1, wherein the defect hosts a lubricant.

3. The method of claim 1, wherein the laser beam is colored in accordance with a wavelength from about 380 nanometers to about 635 nanometers within a visible region of an electromagnetic spectrum.

4. The method of claim 3, wherein the wavelength is about 590 nanometers or less.

5. The method of claim 4, wherein the wavelength is about 570 nanometers or less.

6. The method of claim 5, wherein the wavelength is about 500 nanometers or less.

7. The method of claim 1, wherein the laser beam does not include a red laser beam.

8. The method of claim 7, wherein the laser beam includes a blue laser beam.

9. The method of claim 1, wherein the rotating is a full rotation or less.

10. The method of claim 1, wherein the rotating includes a plurality of full rotations.

11. The method of claim 1, wherein the moving includes pushing the tube.

12. The method of claim 1, wherein the moving includes pulling the tube.

13. The method of claim 1, wherein the computationally acting based on the change includes computationally determining whether the defect satisfies a predefined threshold.

14. The method of claim 1, wherein the computationally acting based on the change includes taking a machine-based action with respect to the tube.

15. The method of claim 14, wherein the machine-based action includes marking the outer side with a mark.

16. The method of claim 15, wherein the mark is in proximity of the defect such that the defect is positionally associated with the mark.

17. The method of claim 14, wherein the machine-based action includes segregating the tube.

18. The method of claim 1, wherein the change is identified based on a reflection beam time difference.

19. The method of claim 1, wherein the computationally acting based on the change includes computationally forming a defect map of the outer side.

20. The method of claim 1, wherein the tube is rectilinear.

21. The method of claim 1, wherein the tube is non-rectilinear.

22. The method of claim 1, wherein the tube varies in cross-section with respect to at least one of a shape or a size thereof.

23. The method of claim 1, wherein the tube is uniform in cross-section with respect to at least one of a shape or a size thereof.

24. The method of claim 1, wherein the tube is an assembly of pieces.

25. The method of claim 1, wherein the defect includes a depression.

26. A method comprising:
   directing a laser beam onto an outer side of a tube, wherein the outer side includes a defect, wherein the laser beam is output via a laser source coupled to a tube straightener;
   rotating the laser beam with respect to the tube such that the laser beam beams onto the defect;
   sensing a reflection of the laser beam from the outer side based on the defect;
   computationally identifying a change between the laser beam and the reflection;
   computationally acting based on the change.

* * * * *